United States Patent [19]

Ewerlöf

[11] Patent Number: 4,869,457
[45] Date of Patent: Sep. 26, 1989

[54] ARRANGEMENT FOR CONTROLLING AND REGULATING A LIQUID FLOWING THROUGH A LINE

[76] Inventor: Göran Ewerlöf, Stenbitsvägen 31, S-181 31 Lidingö, Sweden

[21] Appl. No.: 319,079

[22] Filed: Feb. 27, 1989

[51] Int. Cl.$^4$ .............................................. F16K 7/06
[52] U.S. Cl. ...................................... 251/6; 251/121; 251/205; 137/625.3; 138/43; 138/45; 138/46; 222/564; 604/250; 604/251; 239/569
[58] Field of Search ...................... 251/4, 5, 6, 7, 8, 9, 251/10, 121, 205; 137/625.3, 625.33, 625.42; 138/43, 45, 46; 604/246, 250, 251

[56] References Cited

U.S. PATENT DOCUMENTS

| | | | |
|---|---|---|---|
| 994,167 | 6/1911 | Koppitz | 138/46 |
| 2,129,983 | 9/1938 | Bacon | 604/251 |
| 2,238,677 | 4/1941 | Collins et al. | 251/5 |
| 3,135,259 | 6/1964 | Evans | 251/6 |
| 3,443,609 | 5/1969 | Wehren | 251/5 |
| 3,512,748 | 5/1970 | Wilson | 604/250 |
| 3,574,310 | 4/1971 | Souriau | 251/61.1 |
| 3,814,130 | 6/1974 | Allen et al. | 251/9 |
| 3,831,600 | 8/1974 | Yum et al. | 604/250 |
| 4,406,440 | 9/1983 | Kulle et al. | 251/6 |
| 4,548,598 | 10/1985 | Theeuwes | 604/251 |

FOREIGN PATENT DOCUMENTS 1182016 2/1970 United Kingdom ................ 604/251

Primary Examiner—George L. Walton

[57] ABSTRACT

Arrangement for controlling and regulating a liquid (2) flowing through a line (3). The arrangement comprises a valve body (9) provided with a press-on or deforming element (11) moveable along the line and designed to cooperate with the said line for regulating the flow of the liquid (2), by means of restriction thereof to varying degrees. In the line (3) there is fitted a continuous hollow element (4) having a number of openings (8) through which the said liquid can flow. The press-on element (11) moveable along the hollow element (4) is designed to press the line (3) against the said element (4). By this means a shifting of the press-on element can be carried out such that an optional area of the openings can be uncovered for throughflow since that part of the hollow element where the said area is located is situated on the outlet side in relation to the press-on element. The openings of the hollow element can be uncovered to varying degrees by means of the press-on element arranged in the valve body, the line being pressed against the openings of the hollow element in such a way that the flow is restricted to varying degrees.

6 Claims, 2 Drawing Sheets

4,869,457

ARRANGEMENT FOR CONTROLLING AND REGULATING A LIQUID FLOWING THROUGH A LINE

TECHNICAL FIELD

The present invention relates to an arrangement for controlling and regulating a liquid flowing through a line, which arrangement comprises a valve body provided with a press-on or deforming element movable along the line and designed to cooperate with the said line for regulating the flow of the liquid, by means of restriction thereof to varying degrees, there being fitted in the line a continuous hollow element having a number of openings through which the said liquid can flow.

PRIOR ART

For regulating the flowrate n a line, a plurality of arrangements, particularly valve bodies, of varying complexity are known. In certain areas, for example the medical services, it is desirable to reduce the cost, while retaining a reliable functioning, of the said arrangements. In the medical services a particular type of metering of liquid from a container, a so-called drip, is used to a great extent, for example for intravenous injections. In order to set a suitable flowrate tube clamps are preferably used which grip around the tube and compress the latter to varying degrees. However, this method barely provides the possibility of any more exact setting in view of the fact that the tube material has elastic properties which are altered under the effect of pressure from the tube clamp. After a short time the flow through the tube has been altered and the preset flowrate therefore does not agree with the actual flowrate. There do exist, however, valve bodies for automatic monitoring of the flowrate, but these are of substantially greater complexity and for this reason are not suitable for once-only use.

TECHNICAL PROBLEM

As emerges from the above, there are many problems in accurately regulating a flow in a line over a period of time. No arrangement is previously known by means of which the flowrate in the line can be controlled and regulated by means of interaction with the flexible line and which is not affected by the choice of material for the line.

SOLUTION

The arrangement comprises a valve body provided with a press-on element moveable along the outside of the line, there being fitted in the line, with reference to the position of the press-on element on the line, a continuous hollow element having a number of openings. The press-on element is designed so as to be able to be moved along the line over the hollow element and thus press the line against the hollow element so that an optional area of the openings can be uncovered since that part of the hollow element where the said area is located is situated on the outlet side in relation to the press-on element.

ADVANTAGES

The present invention provides an arrangement for controlling a liquid flowing through a line, which arrangement eliminates the said problems, is simple and inexpensive, and is especially suited for once-only use.

DESCRIPTION OF THE FIGURES

The invention will be described in greater detail below on the basis of an exemplary embodiment, and with reference to the attached drawings in which.

PREFERRED EMBODIMENT

Figure 1:
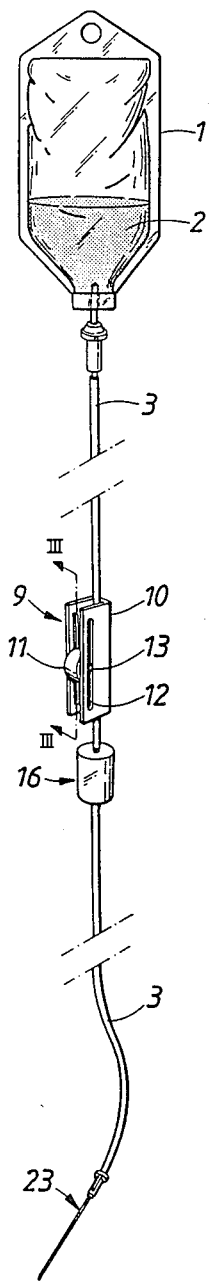
FIG. 1 shows the arrangement with associated liquid container and cannula in perspective.
Figure 2:
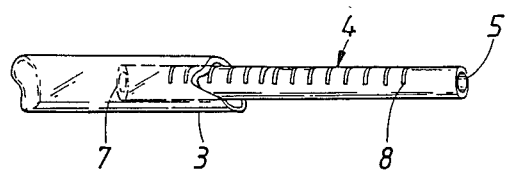
FIG. 2 shows a partly exploded view of the arrangement containing a line and FIG. 3 shows a section, along the line III—III in FIG. 1, of the arrangement.

FIG. 1 shows a view in perspective according to the invention, the embodiment being a drip, principally consisting of a liquid container 1 containing liquid 2 and a flexible tube 3 connected to the liquid container, in which tube a continuous flexible sheath 4 is fitted having a circular sectional area and with its outer diameter smaller than the inner diameter of the tube. As is shown in FIG. 2, the one end 5 of the sheath 4, which end is arranged in the tube opposing the imagined direction of flow of the liquid 2 as indicated by an arrow 6, is sealed off, and the sheath preferably has a conical shape with its smallest diameter at the said end 5 and with its greatest diameter at its opposite end 7 at which the covering surface of the sheath rests against the inner covering surface of the tube and which end 7 is open. Moreover, the sheath 4 has a number of identical openings 8 arranged in sequence and preferably oval in shape, with the longitudinal direction of the openings transverse to the longitudinal direction of the sheath. The openings can also be made of varying size, for example in such a way that the opening nearest to the end 5 of the sheath 4 is smallest, after which the openings are provided with increased size, there being provided regulation of the liquid flow with increased progressiveness.

Figure 3:
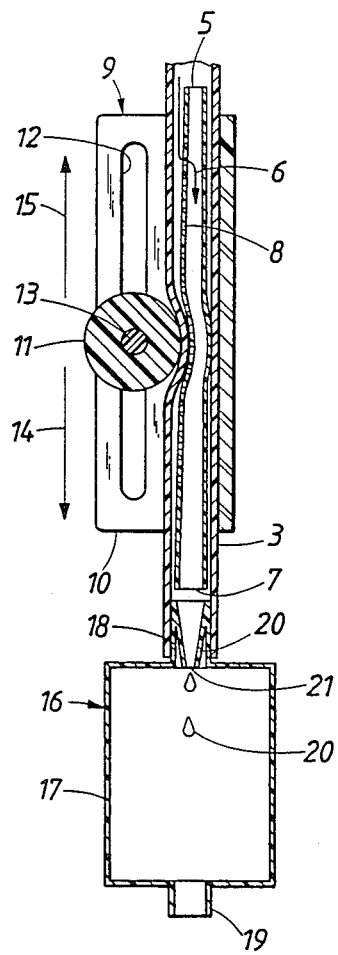

At the section where the sheath 4 is fitted the tube 3 is gripped by a valve body 9, preferably manufactured in a plastic material, which valve body comprises a U-shaped holding fixture 10 having a reel 11 the contact surface of which has a profile matched to the tube, the tube 3 being fitted between the holding fixture and the reel as shown in FIG. 3. The projecting wall parts of the holding fixture 10 each having a continuous recess 12 arranged in the longitudinal direction of the holding fixture, in which recess the reel 11 is rotatably fitted by means of projections 13 arranged on both sides of the reel, in such a way that the reel is slideable in the recesses in both directions which are indicated by arrows 14, 15.

At a section of the tube 3 following the valve body 9 with respect to the imagined direction of flow 6 a drip chamber 16 is arranged which is preferably manufactured in a transparent plastic material and which comprises a container 17 which has two tubular projections 18, 19 extending outwards from the ends of the container, one being intended to act as an inlet 18 and comprising a drip orifice 20 with a hole 21 designed to convert the liquid flow into substantially identical liquid drips 22 and the second projection being intended to act as an outlet 19. The inlet and outlet are inserted in the tube 3 which is thus divided.

As is shown in FIG. 1, at one end of the tube 3 there is attached a long and narrow, tubular needle, cannula 23, preferably made of stainless steel having a low content of nickel in order to eliminate the risk of nickel allergy in patients when the needle is to be inserted and to remain in a vein.

As is shown in FIG. 1, the drip device consists of three main component parts, the liquid container 1, the tube 3 and the cannula 23, in its basic design and is preferably used when a large amount of liquid, for example, blood plasma in cases of acute blood loss, is to be supplied to a patient. To set up a drip the procedure is that the cannula 23 is preferably made to puncture a vein and is inserted into the latter usually by means of a syringe of the conventional type, after which the syringe is removed from the cannula. The free end of the cannula thus projects from the vein, the tube being attached to the cannula preferably by means of some type of socket having friction locking. The cannula is in this connection designed to remain in the vein for the period of time during which the drip is given, and thus the cannula is not replaced when the liquid container is replaced. The liquid flows from the liquid container 1 through the tube 3 to the cannula 23 by means of gravity since the liquid container is positioned higher than the cannula, preferably such that the liquid container constitutes the highest point of the drip device and the cannula its lowest point.

However, the flow of liquid to the patient often has to be controlled more accurately with individual variations so as not to put the patient into a state of shock or to unnecessarily burden the organs of the body. This is made possible by the sheath 4 being inserted in the tube 3 in such a way that the sheath comes to rest with its narrowest end 5 opposing the direction of flow 6, the open end 7 of the sheath resting with one part against the inner covering surface to the tube 3. Thereafter the tube is pressed into the valve body 9 between the U-shaped holding fixture 10 and the reel 11 in such a way that the tube comes to rest in the holding fixture 10 at that part of the tube which comprises the sheath 4, the tube and the sheath being compressed by the reel only to such an extent that the sheath is held in the tube and an open flow channel is maintained through the sheath.

The liquid 2 flows from the liquid container 1 through the tube 3 in the direction of arrow 6 as shown in FIG. 3, the flowing liquid arriving at the sealed-off end 5 of the sheath 4, which end thus functions as a liquid divider. The liquid thus flows round the sheath 4 in order to find a way past the latter, but this is prevented by the reel 11 which compresses the tube and the sheath effectively. The liquid is in this way guided in through the openings 8 and onwards through the sheath. By manoeuvring the reel in the direction of the arrows 14, 15 by rotation of the reel, the latter rolling against the outer covering surface of the tube and being held resting against the latter by means of the projections 13 which run in the recesses 12, the desired number of openings are uncovered by which means the desired flowrate is achieved. The manoeuvring is limited mainly by the length of the recesses 12, so that, when the projections 13 of the reel 11 are in the end position of the recesses in the direction of arrow 15, the reel compresses a part of the end section 5 of the sheath 4 so that the liquid 2 is not allowed to pass through. From this end position the reel can be manoeuvred in the direction of the arrow 14, there being a successively increasing number of openings 8 uncovered so that the rate of the liquid flowing through increases up to a position at the end section 7 of the sheath, the maximum through-flow being achieved when the projections 13 of the reel are in the position corresponding to the second end position of the recesses in the direction of the arrow 14. In the latter position all the openings 8 of the sheath 4 are uncovered.

In order to permit visual detection of the liquid flow for correct control and regulation of the latter by means of the valve body 9, the drip chamber 16 has been arranged downstream of the valve body in respect of the direction of flow 6 of the liquid 2. The tubular projections 18, 19 of the drip chamber 16 are inserted into each of the free ends of the divided tube 3 with the inlet 18 nearest to the valve body, the liquid quantity metered through the sheath being converted into the substantially identical liquid drips 22 by means of the drip orifice 20. This is effected by means of the flow of liquid being compressed in the cone-like drip orifice towards the hole 21, the liquid drips forming and falling into the container 17 so that the number of liquid drips per unit of time can be detected for the said controlling of the restriction of the flow of liquid by means of manoeuvring the reel 11 of the valve body in the direction of the arrows 14, 15.

After the flow of liquid has been converted into the drips 22 the flow of liquid is reformed by means of the drips being collected in the container 17 for further flow through the tube 3 to the cannula 23 which, in the case of intravenous infusions, is partly inserted in a vein of the patient.

As emerges from the above, the arrangement according to the invention consists principally of the sheath 4 which is fitted in the tube 3 in such a way that the liquid 2 flowing in the tube is forced to flow through the openings 8, it being possible to regulate the number of the uncovered openings by means of the valve body 9, the reel 11 of which continuously presses the tube and the sheath together to a certain extent so that the flow of liquid can be restricted to varying degrees.

The invention is not limited to the exemplary embodiment described above and shown in the drawings, but rather can be varied within the scope of the subsequent patent claims. Thus, for example, the sheath can be provided with a flange at its one end, which flange fits tight against the inner covering surface of the tube, it also being conceivable to replace the valve body with a rubber ring which is rolled over that part of the tube where the sheath is fitted. It is also possible to detect automatically the fallen liquid drips by means of photocells placed on both sides of the container, which, via a microprocessor, control for example a small electric motor which automatically manoeuvres the reel in dependence of the fallen liquid drips. Thus, no manual monitoring is required.

I claim:

1. Arrangement for controlling and regulating a liquid (2) flowing through a line (3), which arrangement comprises a valve body (9) provided with a deforming element (11) movable along the line and designed to cooperate with the said line for regulating the flow of the liquid through the line (2), by restricting the line to varying degrees, there being fitted in the line (3) a continuous hollow element (4) having a number of openings (8) through which the said liquid can flow, characterized in that the deforming element (11) is moveable along the line (3) and is designed to press the line (3) against said element (4) so that, by means of shifting of the deforming element along line (3), a selected number of the openings can be uncovered for a variable through-flow since that part of the hollow element where the selected number of openings is located is situated on the inlet side in relation to the positioning of the deforming element along line (3) since the deforming element (11) presses line (3) against element (4).

2. Arrangement according to claim 1, characterized in that the line is made up of a flexible tube (3) in which the continuous hollow element (4) is fitted, in that the said hollow element is preferably made up of a sheath (4) of flexible material provided with openings (8) and which tube and sheath are compressed to a certain extent by means of a clamping body (11) included in the valve body (9) and forming the said deforming element.

3. Arrangement according to claim 2, characterized in that the sheath (4) is preferably conical in shape with its narrowest part directed against the inflowing liquid, in that one end (5) of the sheath is sealed and in that its opposite end (7) is open, the openings (8) being designed to act as inlets and the open end (7) of the sheath being designed to act as an outlet so that a through-flow channel is formed through the sheath for the liquid (2) flowing in the tube (3).

4. Arrangement according to Claims 2 or 3, characterized in that the clamping body is preferably made up of a reel (11) provided with projections (13) and which reel is rotatably arranged in recesses (12) in a U-shaped holding fixture (10), the tube (3) and the sheath (4) being compressed between the reel and the holding fixture.

5. Arrangement according to claim 1, characterized in that a collecting body (16) is connected to said line and comprises a metering element (20) which converts the liquid flow into liquid drips (22) and which is arranged on a container (17) which has at least one inlet (18) and one outlet (19).

6. Arrangement according to claim 5, characterized in that it is designed to be used in connection with intravenous infusion in order to convert, by means of the collecting body (16) connected to the line (3), the flow of liquid present therein to a sequence of substantially identical falling liquid drips (22) for collection of the latter for the purpose of reforming the liquid flow.

* * * * *